United States Patent
Ferguson et al.

[11] Patent Number: 6,045,813
[45] Date of Patent: Apr. 4, 2000

[54] LOTIONS AND GELS WITH ACTIVE INGREDIENTS IN BEADS

[75] Inventors: John Ferguson, Westerville; George Ziets, New Albany, both of Ohio

[73] Assignee: Bath & Body Works, Inc., Reynoldsburg, Ohio

[21] Appl. No.: 09/050,536

[22] Filed: Mar. 30, 1998

[51] Int. Cl.[7] .............................. A61K 7/00; A61K 7/021; A61K 9/48; A61K 9/50
[52] U.S. Cl. ........................... 424/401; 424/63; 424/451; 424/455; 424/452; 424/489; 514/844; 514/846; 514/847; 514/951; 514/952
[58] Field of Search ..................... 424/451, 455, 424/456, 401, 489, 63, 452; 428/402.2

[56] References Cited

U.S. PATENT DOCUMENTS 5,089,269  2/1992  Noda et al. .............................. 424/456

*Primary Examiner*—James M. Spear
*Attorney, Agent, or Firm*—Colucci & Umans

[57] ABSTRACT

A flowable personal care or cleaning composition, comprising a carrier and friable beads disbursed in the carrier, the beads containing an active ingredient and enclosing the active ingredient in a wall of bead material, the active ingredient amounting to approximately 0.5–5.0% by weight of the bead including its wall material and the active ingredient.

20 Claims, 3 Drawing Sheets

LOTIONS AND GELS WITH ACTIVE INGREDIENTS IN BEADS

FIELD AND BACKGROUND OF THE INVENTION

The present invention relates, in general, to skin care and household products, and in particular, to a new and useful gel or lotion which can be used for such things as sanitizing the hands, moisturizing and adding fragrance to the skin, a shampoo, a liquid soap product, a household cleanser and the like, which includes active ingredients such as antibacterial agents or essential oils, which are captured within friable beads.

The use of microencapsulation is known in various fields. Microencapsulation involves the capturing of active ingredients within a shell which can be broken or dissolved, depending on the environment in which the active ingredient is to be released. Generally, however, microencapsulation has been utilized in the pharmaceutical and quasi-pharmaceutical field, to time release medication, vitamins or minerals by encapsulating the active ingredient within a shell which dissolves over time in the stomach.

The use of encapsulated materials to control release and improve the stability of composition is well established. Encapsulation efficiency can be improved by reducing the relative percentage of the protective wall material and increasing the quantity of the core encapsulate. Emphasis has been place on maximizing the absolute delivery of the encapsulated core material. The present invention teaches the use of macro capsules (500–1,500 microns) as a way to visually mark the coverage of personal care, household and pharmaceutical preparations. Further, this invention teaches a very low concentration of core material (0.5% to 5.0%) is an effective way to provide controlled release and visual indication of product coverage, which is contrary to general teaching in this field. The present invention can also be used to mix incompatible, quasi-compatible or complimentary ingredient (carrier formula and beads contents) at the time of use.

SUMMARY OF THE INVENTION

An object of the present invention is to take advantage of rupturable beads in a liquid gel or lotion, which contain small amounts of active ingredients for use in cleansing, treating or adding fragrance to the skin of a user or for other household uses.

According to the present invention, the beads may contain either an antiseptic such as Triclosan, or essential fragrance oils, referred to as essential oils, for imparting fragrance and/or other active ingredients to the skin such as moisturizers and the like, or as cleansers for other surfaces.

It was found by the inventors that the use of beads which were too flexible would allow the beads to survive the manufacturing process, but the beads would not then readily break when the lotion or gel was rubbed onto the skin. One hurdle which was overcome by the present invention was to utilize beads of proper diameter and wall thickness which did not rupture during the manufacturing process, but, after a 24 to 48 hour induction period were friable (pulverizable or rupturable) when the lotion or gel was rubbed onto the skin or dispensed through a restrictive orfice. It was found that beads that contained only about 0.5 to about 5% by weight active ingredient and which are mostly wall material, could be used according to the present invention and in fact, added an additional advantage in that the wall material could contain coloring which would act as an indicator to the user both that enough of the active ingredient was present on the hands or surface and secondly, that the active ingredient has been released in that the color would smear, indicating rupturing of the beads.

The use of beads also permitted the inventor to utilize a dual fragrance system. One fragrance is in the carrier lotion which carries the beads. This fragrance is tailored to be pleasant when exposed to the air. Another different fragrance, however, was used with the active ingredient in the beads, in particular, in the version of the invention for dispensing essential oils to the skin. This different fragrance was selected both to give a different scent, but also to be of the type of fragrance which is best activating when coming into contact with the skin. It is known in the field of fragrances that some fragrances are more effective as "room fresheners" and others are more effective as "perfumes" in that they are more active and have different advantageous effects when applied to the skin. By providing the active ingredient with the skin compatible fragrance in the beads, two separate fragrances could be utilized in the product, and fragrances which were tailored for their particular use, that is, either to give out a fragrance simply upon contact with the air or to give out a fragrance best when in contact with the skin.

The lotion and gels of the present invention whether for containing the essential oils or the antibacterial agent, have preferred approximate diameters of about 500 to 900 microns with a wall thickness of about 210 to 440 microns.

Compositions in the form of a shower gel containing beads with essential oils, are generally about 1000 to 1500 microns in diameter with a wall thickness of about 460 to about 740 microns.

Despite the relatively small volume within the bead wall, which is available for containing the antibacterial agent or essential oil at a rate of only about 0.5 to about 5% by weight of the overall bead, sufficient active ingredient is present to satisfy the purpose of the invention and also to add the indicating function and provide sufficiently robust beads. Accordingly, the seeming disadvantage of having beads with very large wall thicknesses, is more than compensated by the other advantages of indication and friability characteristics.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
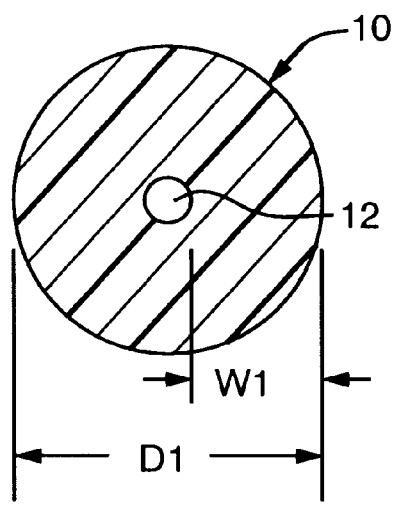
FIG. 1 is a cross-sectional view of a bead for containing an active ingredient and for use in a lotion composition of the present invention.

Referring to the drawings, FIG. 1 illustrates a bead generally designated 10 in accordance with the present invention having a diameter D1 of about 500 to 900 microns and a wall thickness W1 of about 210 to 445 microns. Although these measurements are approximations, they are representative and illustrate the fact that bead 10 is mostly wall thickness with only a very small, roughly spherical volume 12 remaining to contain the active ingredients whether it is the antibacterial agent or the essential oils of the present invention. By weight, bead 10 is about 98 to 99.5% wall material and only about 0.5 to about 2% active ingredient in volume 12.

These dimensions are representative for the beads used in the lotions of the present invention, both the essential oil containing lotion referred to as an "Aromatherapy" lotion, and an antibacterial lotion containing Triclosan or other antibacterial agent.

Figure 2:
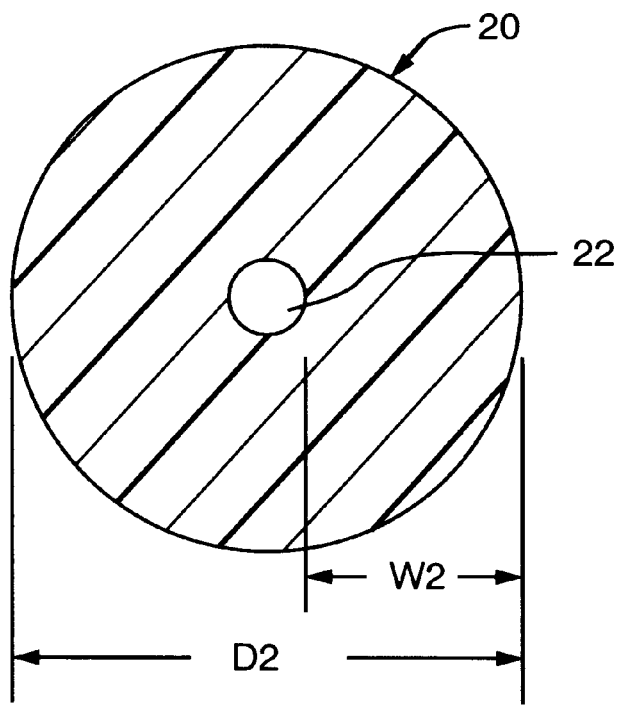
FIG. 2 is a view similar to FIG. 1 of another embodiment of the bead for use with a gel of the present invention.

FIG. 2 illustrates a bead generally designated 20 useful in gels of the present invention such as shower gels and shampoo gels. In this embodiment, the diameter D2 is about 1000 to 1500 microns and the wall thickness W2 is about 420 to 740 microns. This also leaves a volume 22 for containing only about 0.5 to about 5.0% by weight active ingredient, the bead being mostly inert wall material.

Although intuitively, this would appear to be a disadvantage in that very small amounts of active ingredients are present, in fact, the thick walls of the beads compensate any disadvantages by providing the advantages of dual fragrance capabilities and beads which are not friable during the manufacturing process involving mixing together and loading of the lotions or gels into bottles. The beads, after a 24 to 48 hour introduction period, do become friable when they are massaged into the skin or scalp, however, causing the beads to break and thus releasing their active ingredients in sufficient quantities to have the desired effects. In addition, the wall material can contain a harmless non-toxic colorant which is water soluble or water disbursable and which adds to the effect of the invention by providing a visual que to the amount of active ingredient being worked into the skin and also the fact that sufficient mechanical massaging has taken place to activate the ingredients by rupturing the beads and smearing to color. The beads, in effect, rupture and smear across the skin, releasing the active ingredient. The bead material is easily washed away with water, however, so that no adverse effect occurs. For example, a white, yellow or pink translucent or clear lotion or gel may contain blue or green color beads.

Another use of the invention involved a hydro alcoholic solution capable of dispensing a fragrance or providing an effective disinfective alcohol concentration to the skin or a hard surface. In this application, the encapsulated bead breaks inside the pump mechanism, intimately mixing and coloring the solution. Thus a clear solution with colored beads dispensed throughout can be dispensed onto the skin as a colored product. This can be used for both aesthetic purposes and functionally to mark product placement on the skin or some other surface.

An example of the shower gel has the following approximate composition and range of amounts:

TABLE 1

| Ingredient | Representative Amount | Range |
| --- | --- | --- |
| Water | 45 | 35–70 |
| Thickener | 1.2 | 0.5–5 |
| Surfactant | 36 | 12–40 |
| Fragrance | 2 | 0.5–3 |
| Emollient | 2 | 0.5–5 |

An example of a lotion according to the present invention is:

TABLE 2

| Ingredient | Representative Amount | Range |
| --- | --- | --- |
| Water | 80 | 40–90 |
| Emulsifier | 4 | 3–10 |
| Emollient | 10.75 | 2–10 |
| Botanicals | 0.7 | 0.1–1 |
| Fragrance | 1.0 | 0.2–3 |
| Triclosan | 0.3 | 0.1–1 |

In the lotion, the beads amount to approximately 0.5 to 2.0% by weight of the overall composition and in the gel, the beads amount to 0.5 to 1.0% of weight of the overall composition.

To be effective, the wall material must be colored and possess sufficient strength to withstand normal manufacturing mixing, pumping and filling operations. In use, the wall material must be friable enough to break easily with hand pressure or implement (cloth, sponge or paper) wiping.

Ideally, the macro capsule should have an impervious wall material in the dry state and gradually soften in the cleaning, cosmetic or pharmaceutical preparation. This characteristic allows the capsules to be processed fresh, in a hardened state, and become friable when equilibrium is established with the preparation.

Capsule breakage can be accomplished by hand or implement pressure after the preparation has been dispensed. It can also be fractured at the time of application by dispensing the preparation through a mechanical pump or restricted orifice. This latter technique allows the colored wall material and its encapsulate core to intimately mix with the preparation at the precise moment of use. The resultant product is colored and provides strong visual indication of its coverage.

If the internal clearances of the pump are smaller than the D1 or the D2 in FIGS. 1 and 2 herein, the cross sectional diameter of the bead, it will rupture inside the pump and intimately mix with the rest of the formula. This could lead to the mixing of two quasi-compatible or incompatible ingredients (formula and bead) to produce neutralization, heat, color or some other chemical reaction.

After the beads are placed in solution (aqueous or hydroalcoholic) the wall slowly softens and becomes friable. This induction period is dependent upon time, temperature and the surface activity of the formula. For the examples, this induction period is 24 to 48 hours at room temperature.

The following examples demonstrate the utility of the invention across three broad product categories: pharmaceutical, personal care and cleaners. These examples also demonstrate the importance of the induction period to produce friability. Finally, the examples demonstrate the bead release mechanics, via hand or implement wiping and internal breakage, via mechanical dispensing.

In all of the applications cited, the 500 to 1500 microns (31 thousandths to 58 thousandths of an inch) cellulose, lactose, hydroxypropyl methyl cellulose spherical macro beads identified by the trademark UNISPHERES manufactured by Induchen AG of Dubendorf, Switzerland and with the generalized formula listed below were added to the formula last. The formulas were then transferred by pouring, (for laboratory preparations), or by pumping, (for commercial preparation), to their final containers. Standard diaphragm or displacement pumping equipment can be used so long as the beads have not passed through their induction period; i.e. when first added to the formula they are not shear sensitive as defined by the examples described below.

TABLE 3

Generalized Bead Composition

| Material | % by weight |
|---|---|
| Lactose | |
| Cellulose | |
| Hydroxypropyl Methyl Cellulose | 98 |
| Color | |
| Perfume or triclosan | 2 |
| | 100 |

TABLE 4

Anti-Bacterial Water in Oil Lotion Formulas

| Material | A | B | C | D | E | F | G | H | I | Function |
|---|---|---|---|---|---|---|---|---|---|---|
| Water | QS | QS | QS | QS | QS | QS | QS | QS | QS | Carrier |
| Triclosan | 0.3 | 0.3 | 0.3 | 0.3 | 0.3 | 0.3 | 0.3 | 0.3 | 0.3 | Biocide |
| Glycerin | 5.0 | 5.0 | 5.0 | 5.0 | 5.0 | 5.0 | 5.0 | 5.0 | 5.0 | Humectant |
| Stearic Acid | 3.0 | 3.0 | 3.0 | 3.0 | 3.0 | 3.0 | 3.0 | 3.0 | 3.0 | Emulsifier |
| Triethanol Amine | 0.3 | 0.3 | 0.3 | 0.3 | 0.3 | 0.3 | 0.3 | 0.3 | 3.0 | Neutralizer |
| Cetyl Alcohol | — | — | 0.75 | 0.75 | 0.75 | 0.75 | 0.75 | 0.75 | 0.75 | Emulsifier |
| Glycol Stearate | — | — | 3.5 | 3.5 | 3.5 | 3.5 | 3.5 | 3.5 | 3.5 | Emollient |
| Dimethicone | — | — | 0.25 | 0.25 | 0.25 | 0.25 | 0.25 | 0.25 | 0.25 | Occlusive Agent |
| Wheat Germ Oil | — | — | — | 0.4 | 0.4 | 0.4 | 0.4 | 0.4 | 0.4 | Conditioning Agent |
| Panthenol | — | — | — | — | 0.1 | 0.1 | 0.1 | 0.1 | 0.1 | Conditioning Agent |
| Perfume, Apple | — | — | — | — | — | — | 1.0 | 1.0 | 1.0 | Fragrance |
| F, D, & C Yellow 6 | — | — | — | — | — | — | — | — | 0.001 | Colorant |
| Ultramarine | — | 1.0 | — | 1.0 | — | 0.5 | — | 0.75 | 1.0 | Biocide, |
| Blue Beads | | | | | | | | | | Visual Indicator |
| | 100 | 100 | 100 | 100 | 100 | 100 | 100 | 100 | 100 | |

Examples A through H (Pharmaceutical Application): Various triclosan containing anti bacterial oil in water emulsion were prepared by dispensing an aqueous phase into the oil phase and mixing until uniform. Color, fragrance, and skin conditioning agents were added to modify the preparation for various applications.

The product in example A is an opaque white emulsion. When applied to the skin it is difficult to visually gauge product coverage. Product from example B, containing the lactose-cellulose beads was placed in a tube and in two 8 oz. PVC plastic bottles fitted with commercially available dispensers, one of which is FIG. 3. This and other suitable dispensers are available from Calmar Inc. of City of Industry, Calif.

Within an hour of preparation and filling, it was attempted to dispense Example B from another lotion pump dispenser with small complex internal passages. The beads quickly clogged the dispenser and product could not be dispensed. Product B was also dispensed form the bottle using the high volume of FIG. 3 pump. This time the product dispensed easily and the individual blue beads were readily observed in the white lotion. However, like the Product B dispensed from a tube, the beads were hard and could not be broken by hand rubbing.

Product or Example B was then allowed to remain at room temperature for 48 hours. After this induction period, product dispensed from the tube quickly broke under hand pressure. The presence of the blue colored beads clearly marked where the lotion had been dispensed. When the lotion was spread onto the skin, the hand pressure caused the blue colored beads to quickly break citing a trail of color which designated to the user product coverage. As the lotion was rubbed into the skin, the blue dissipated and left no recognizable color on the skin.

Figure 3:
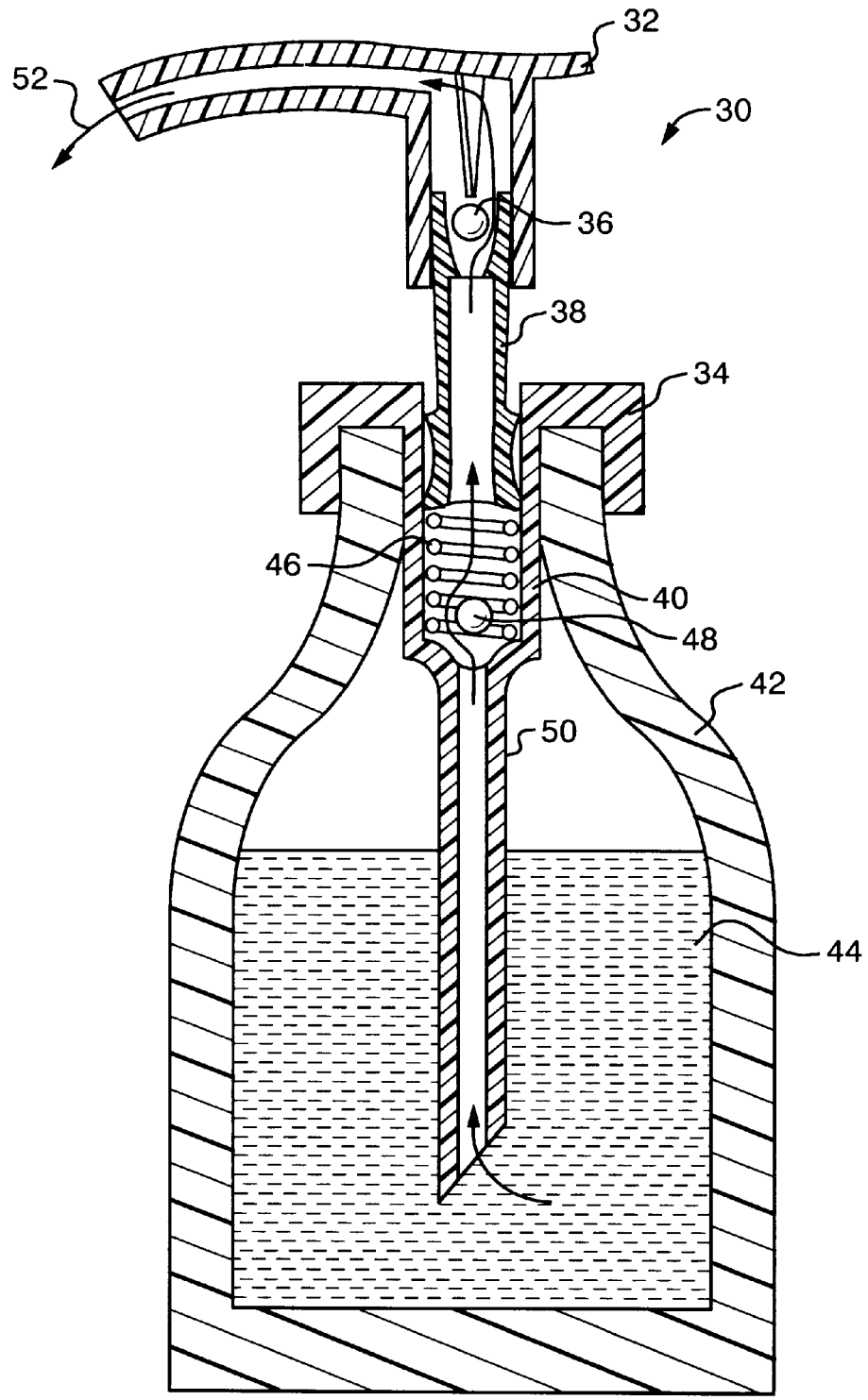
FIG. 3 is a schematic sectional view of a dispenser for lotions and gels which can be used to dispense the composition of the present invention and to practice the method of the present invention.

In a similar fashion, after 48 hours at room temperature, the product in Product B was dispensed through each of the two Calmar dispensers previously described. The results are described below. The pump of FIG. 3 is a high volume pump (0.8 to 1.2 g per actuation) and has internal tolerances greater than be cross-sectional diameter of the bead. That is the blue beads passed through the pump mechanism without breaking and was dispensed onto the skin as a white lotion with discrete blue beads dispensed throughout, As with the product dispensed form the tube, the white lotion with blue beads quickly broke with hand pressure, marked where the lotion had been, and quickly faded away leaving no recognizable color.

The other Calmar pump (a model MD-150) is a low volume pump (0.10 to 0.25 g per actuation) with internal tolerances smaller than the cross-sectional diameter of the beads. When dispensed, the internal pump mechanism in the MD-150 broke the beads, mixed them with the dispersed phase and the product exited the pump as a light blue homogeneous lotion. That is, the blue beads broke inside the pump at the discharge valve inside the spin chamber and mixed into the white lotion to produce a single-phase light blue lotion. The light blue lotion was easily discernable on the skin and quickly dissipated as it was rubbed into the skin. In a similar fashion, the product example pairs described by C/D, E/F and G/H behaved in the same fashion. The white lotions in C, E and G were functional but did not provide the user with a clear indication of product location or coverage. The white lotion with blue beads; D, F and H, after a 48 hour induction period, could be dispensed as an intack discrete two component system through a tube or a mechanical pump; e.g. the Calmar pump of FIG. 3 whose internal pumping tolerances or final restriction metering orifices were greater than the cross-sectional diameter of the beads. If the pump tolerances of final metering orifices were less than the cross-sectional lead diameter, the blue Triclosan beads broke and thoroughly mixed together to produce a homogenous single light blue lotion. The color of lotion could be easily adjusted by varying the concentration of blue Triclosan beads in the final formula. The higher the bead concentration, the more intense the homogeneous blue color.

This discovery also permits the preparation of two chemically incompatible ingredients to exist together in either the continuous lotion phase or dispersed bead phase. To demonstrate this, a small amount of F, D & C Yellow No. 6 was added to preparation H to produce Example I, a light yellow lotion with blue beads. When dispensed from a tube or a bottle fitted with a FIG. 3 pump, after the 48-hour induction period, the user could readily observe on the skin a light yellow lotion with blue Triclosan beads. This turned into a light green lotion as the hand pressure broke the beads and the blue and yellow mixed together. If a Calmar MD-150 pump is used, the light yellow lotion with blue Triclosan beads in the bottle will dispense as a homogenous light green lotion because the internal pump mechanism will beak the blue beads and thoroughly mix them with the yellow lotion.

To further demonstrate the utility of this invention, the following examples are listed in Table 5 below. In all cases the beads were added to formula G for 24 to 48 hours before the experiment was conducted.

TABLE 5

Anti Bacterial Oil in Water Lotion Formulas
Encapsulated Bead Color Dispensing Options

| Experiment | Appearance Before Dispersing | Calmar Dispenser | Appearance After Dispensing |
| --- | --- | --- | --- |
| 1. Formula G + 1% blue beads | White Lotion with Blue Beads | MD-150 | Uniform Light Blue Lotion |
| 2. Formula G + 6% blue beads | White Lotion with Blue Beads | MD-150 | Uniform Dark Blue Lotion |
| 3. Formula G + 1% blue beads and 1% yellow beads | White lotion with Blue and yellow beads | MD-150 | Uniform medium Green Lotion |
| 4. Formula G + 1% blue beads | White lotion with purple beads | MD-150 | Uniform medium Purple Lotion |
| 5. Formula I | Yellow Lotion with Blue Speckles | MD-150 | Uniform medium Green Lotion |
| 6. Formula I | Yellow Lotion with Blue Speckles | FIG. 3 | Yellow lotion with Blue Speckles which Formed a Medium Green Lotion When Rubbed into the Skin. |

These experiments indicate a wide variety of colors and intensities can be created by either dispersing the appropriate concentration of colored beads in a white lotion or adding the appropriate concentration of colored beads to a colored lotion. The color can be created by fracturing the friable beads in the internal mechanical dispensing device when the pump tolerances are smaller than the cross sectional bead diameter. Alternately, the color can be created in situ on the skin or other hard surface by dispensing the preparation through a tube or mechanical dispenser with internal metering tolerances greater than the cross sectional bead diameter.

Those skilled in the art would readily recognize this discovery is also applicable to encapsulating one or more chemically reactive species within a bead and uniformly mixing the ingredient into the preparation at either the moment of mechanical dispensing or upon hand and/or implement pressure as the preparation is rubbed into the skin.

In each of the foregoing formulas and experiments, the presence of the colored ultramarine blue beads containing the triclosan active provided the user with a visible marker that the antibacterial preparation was being correctly and uniformly applied to the treated area. This is especially helpful to users where under application could create secondary infection or over application could create undue surrounding tissue trauma.

This invention is also applicable to other uses such as disinfecting hand surface cleansers and personal care products where visible indication of product coverage or specialized encapsulation of ingredients are important for performance and functionality.

TABLE 6

Disinfecting Hard Surface Cleaner Formulas
Percent by Weight

| Material | J | K | L | M | Function |
| --- | --- | --- | --- | --- | --- |
| Ethyl Alcohol | 65 | 65 | 65 | 65 | Anti Microbal |
| Water | QS | QS | QS | QS | Solvent |
| Diisopropyl Amine | 0.5 | 0.5 | 0.5 | 0.5 | Neutralizer |
| Carbopol 941 | 0.35 | 0.35 | 0.35 | 0.35 | Thickening/ Suspending Agent |
| Aloe Vera Gel | — | — | 0.5 | 0.5 | Moisturizer |
| Perfume, Apple | — | — | 1.0 | 1.0 | Fragrance |
| Ultramarine Blue | — | 0.5 | — | 1.0 | Biocide, Visual Indicator |
| Triclosan Beads | 100 | 100 | 100 | 100 | |

Formulas J through M are transparent, thickened, alcohol gels with viscosities of 5,000 to 8,000 cps. Formulas J and K are suitable hard surface disinfectant formulas suitable for kitchen and other food contact sanitization applications. They are also disinfectant products for bathroom and other hard surface articles such as doorknobs, shopping cart handles and telephone receivers. The formulas were made by dispensing the Carbopol 941 into water, neutralizing it with diisopropylamine and adding the alcohol. Perfume moisturizer and/or Triclosan beads were subsequently added.

Figure 4:
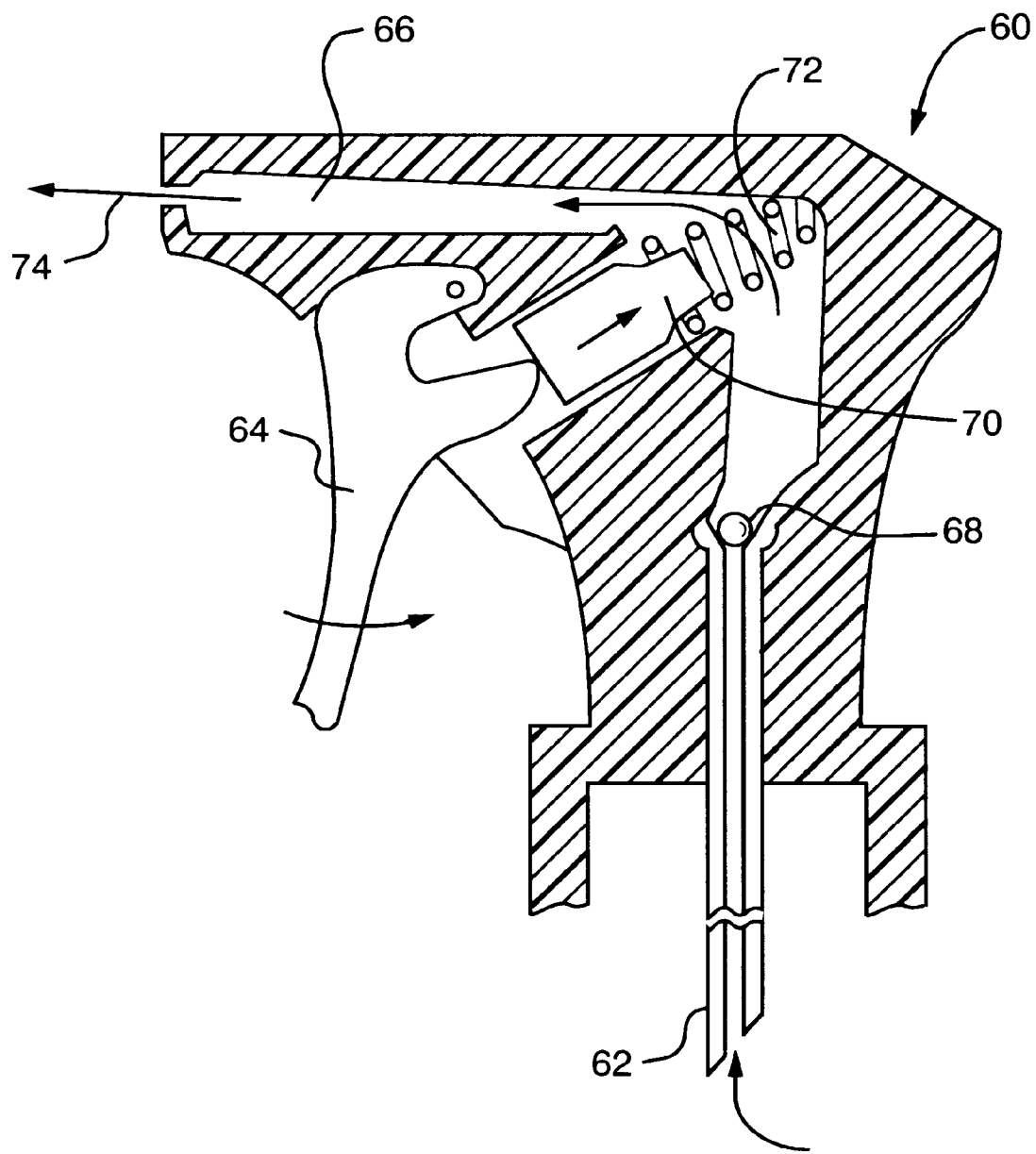
FIG. 4 is a schematic sectional view of a sprayer mechanism which can also be used to dispense the composition of the present invention and in accordance with the method of the present invention.

The triclosan containing blue beads were added to formulas K and M and used within 30 minutes of preparation and after a 24 hour induction period. Formula K was dispensed with a trigger spray pump fabricated with a transparent plastic housing as shown in FIG. 4. This device was chosen because the blue beads could be visually observed during the dispensing operation.

Formula J, when sprayed onto a white enameled surface, was difficult to visually observe for coverage. Ultramarine blue triclosan beads were added to produce Formula K. When sprayed through the trigger spray pump within thirty minutes of preparation the pump quickly clogged. Visual inspection of transparent pump mechanism revealed the beads had become lodged in both the dip tube leading to the piston chamber and in the piston chamber itself. Both areas were full of unbroken beads, rendering the pump nonfunctional. After 24 hours, Formula K was transferred to a new bottle and a new trigger spray pump of FIG. 4 was attached to the bottle. The formula easily dispensed through the pump. Visual inspection of the pump indicated the piston chamber contained a clear light blue homogenous solution indicating the clear continuous phase of the alcohol sanitizer had thoroughly mixed with the ultramarine triclosan beads. When sprayed onto a white enameled surface, a light blue solution was readily observed. This light blue solution was easily wiped away with a paper towel yielding a clean, disinfected surface.

Formula L an instant hand sanitizer, was poured onto the hands and rubbed into the skin. Product coverage was difficult to observe. Formula M was poured onto the hands within 30 minutes of preparation. A clear alcohol gel containing bright blue speckles was readily observed. The formula when rubbed into the hands, was very uncomfortable. The beads were hard and granular and could not be broken with hand pressure. After 24 hours, Formula M was poured into the hands. The transparent alcohol gel containing blue speckles easily fractured with hand pressure marking where the product had been applied. The formula easily rubbed into the hands and left no observable color.

Formulas N through Q are transparent, thickened, surfactant cleaning solution with viscosities of 8,000 to 20,000 cps. As in the previous examples, the lactose/cellulose beads described in Table 3 required a 24 to 48 hour induction period before the beads became friable and easily broken by mechanical, hand or implement pressure. The colored lactose/cellulose beads used in Formulas O and Q contained a 100% active perfume oil specifically designed to be substantive to the skin. This encapsulated oil was different from the bulk fragrance in the shower gel. Bulk fragrances must be specifically formulated to be compatible with the preparation. They are incorporated into the final product with solvents or emulsifiers to yield homogenous solutions or dispersions. Since most of the perfume will be either rinsed, wiped or washed away, it is a very inefficient process to directly apply perfume to an absorbent substrate such as skin and retain lasting fragrance benefit from the absorbed perfume. Furthermore, the only fragrance effect that can be created is that fragrance which comes from the bulk perfume in the formula.

The examples listed in Table 7 demonstrate the ability to formulate a dual fragrance personal care product. This invention permits the user to experience both the fragrance from the bulk product during the shower or bathing activity and the same or different fragrance directly apply to the skin from a friable encapsulated fragrance bead. This produces a longer lasting fragrance benefit.

TABLE 7

Bath and Shower Formulas
Percent by Weight

| Material | N | O | P | Q | Function |
|---|---|---|---|---|---|
| TEA Laurel Sulfate | 18.0 | 18.0 | 18.0 | 18.0 | Surfactant |
| Water | QS | QS | QS | QS | Solvent |
| Carbopol 2020 | 1.2 | 1.2 | 1.2 | 1.2 | Thickener |
| Carboxtmethylcellulous | 0.1 | 0.1 | 0.1 | 0.1 | Suspending Agent |
| Triethanol Amine | 1.3 | 1.3 | 1.3 | 1.3 | Neutralizer |
| Propylene Glycol | 5.0 | 5.0 | 5.0 | 5.0 | Rheology Control |
| Ethyl Alcohol | 4.0 | 4.0 | 4.0 | 4.0 | Rheology Control |
| Carbowax 400 | 0.9 | 0.9 | 0.9 | 0.9 | Emulsifier |
| Citric Acid | 0.1 | 0.1 | 0.1 | 0.1 | pH Control |
| Silicone Fluid | 2.0 | 2.0 | 2.0 | 2.0 | Moisturizer |
| Germaben II | 1.0 | 1.0 | 1.0 | 1.0 | Preservative |

TABLE 7-continued

Bath and Shower Formulas
Percent by Weight

| Material | N | O | P | Q | Function |
|---|---|---|---|---|---|
| Fragrance: | | | | | |
| H&RA3025OR | 2.0 | 2.0 | 2.0 | 2.0 | Perfume |
| D&C Violet #2 | 0.007 | 0.007 | 0.007 | 0.007 | Colorant |
| Aloe Vera Gel | — | — | 0.1 | 0.1 | Moisturizer |
| Chamomile Extract | — | — | 0.1 | 0.1 | Skin Softener |
| Purple Fragrance Beads H&R A3050D | — | 0.5 | — | 0.5 | Substantive Skin Fragrance and Visual Indicator |

Formula N and O were dispensed onto a wash cloth and spread over a wet forearm. Both products foamed and cleaned the skin. Formula O, with the purple fragrance beads provided a clear visual marker on the skin and were easily broken by rubbing them with the wash cloth.

To demonstrate the advantages of having a separate, skin substantive fragrance in a macro capsule bead, the following experiment was conducted with formulas P and Q. As noted in Table 7, the only difference between the two formulas is the 0.5% by weight of the violet bead containing the skin substantive fragrance H&R A 30550D which was different from the fragrance H&R A 30250R in the bulk product.

A test subject placed 15 g of Formula P on his moistened left arm and lathered the arm for 15 seconds with his hand. The arm was then thoroughly rinsed for 60 seconds with 95° F. tepid water from a fast flowing faucet (1.5 to 2.0 gallons per minute). The arm was patted dry with an unperfumed paper towel. In an identical fashion, 15 g of formula Q was applied to the right arm, lathered, rinsed and dried. The purple fragrance beads readily ruptured with hand pressure during lathering. After 15 minutes, one hour and four hours, independent evaluators were asked to smell the right and left forearm and rate each for residual fragrance intensity. The results are summarized in Table 8 below. To minimize any possible first smelled bias by the evaluators, alternate forearms were smelled first. Evaluators were allowed to rate one forearm more intense than the other or rate both forearms equal in fragrance intensity.

TABLE 8

Fragrance Intensity on Treated Forearm

| Time | No. of Evaluators | P Formula More Intense | Q Formula More Intense | No. Differences |
|---|---|---|---|---|
| 15 min. | 5 | 0 | 4 | 1 |
| 60 min. | 3 | 0 | 3 | 0 |
| 240 min. | 3 | 0 | 3 | 0 |

After 15 minutes, one evaluator rated both arms equally intense, while four rated the one treated with Formula Q more intense. Subsequent longer time evaluation indicated the special skin substantive fragrance contained in Formula Q was always more intense.

The use of such macro beads to deliver other cosmetic and medical treatments to the skin would be known to those skilled in the art.

The pump dispenser generally designated 30 in FIG. 3 is of known design and includes a saddle head 32 which can be pushed down with respect to a closure or cap 34, to raise a first ball valve 36 and move a piston 38 downwardly in a cylinder 40 which is connected to a container 42 for containing the lotion, gel or other viscous composition 44 according to the present invention. Downward pumping action is resisted by a return spring 46 which engages around a second ball valve 48 which rises to allow fluid from the container 42 to rise in an inductor tube 50, past valve 48 and spring 46 up through a hollow interior channel in piston 38, and through the interior of head 32 to be dispensed at 52. With the internal diameters of inductor 50 and piston 38 and the geometry of ball valves 36 and 48 selected so that the fluid never passes through a constriction of less than the diameter of the largest beads in the composition, the beads will not rupture but will pass with the surrounding fluid in the direction of arrow 52. Conversely, if a pump dispenser is selected which has internal passages of smaller diameter, the beads will rupture allowing the contents of the beads to mix with the surrounding vehicle thus dispensing a colored mixture at 52.

FIG. 4 illustrates the conventional spray dispenser generally designated 60 which can also be used in accordance with the present invention for more fluid compositions which rise through a supply tube 62 during an initial priming step when the trigger 64 is pumped a few times to discharge air from an outlet conduit 66 to fill the conduit with the composition of the present invention. The composition is trapped in the passage 66 and its communicating passages, by a ball valve 68 and is dispensed by a piston 70 which is pushed inwardly against the action of a return spring 72, to dispense fluid from passage 66 in the direction of arrow 74.

While specific embodiments of the invention have been shown and described in detail to illustrate the application of the principles of the invention, it will be understood that the invention may be embodied otherwise without departing from such principles.

What is claimed is:

1. A flowable composition, comprising:

a carrier; and visible friable beads disbursed in the carrier, the beads containing an active ingredient and enclosing the active ingredient in a wall of bead material, the active ingredient amounting to approximately 0.5–5.0% by weight of the bead including its wall material and the active ingredient and including colorant in the wall material of the beads, the wall material being selected to be non-friable when exposed to a process for mixing the beads with the carrier.

2. A composition according to claim 1 wherein the active ingredient comprises bactericidal liquid.

3. A composition according to claim 1 wherein the active ingredient comprises at least one essential fragrance oil.

4. A composition according to claim 1 wherein the friable beads are maintained in the carrier for at least about 24 to 48 hours before the composition is used.

5. A composition according to claim 4 wherein the beads are from about 500 to about 1,500 microns in diameter and the wall thickness of the beads is between about 210 and 740 microns.

6. A composition according to claim 5 wherein the active ingredient comprises antibacterial liquid.

7. A composition according to claim 5 wherein the active ingredient comprises essential fragrance oils.

8. A composition according to claim 1 wherein the carrier contains one fragrance and the active ingredient comprises a different fragrance.

9. A composition according to claim 8 wherein the different fragrance in the beads is a skin activated essential fragrance oil, the fragrance in the carrier being a bulk fragrance.

10. A composition according to claim 1 wherein the active ingredient is selected from the group consisting of fragrance, bactericidal liquid, a pharmaceutical, a skin moisturizer and a cleanser, the carrier having a different color from the colorant in the wall material of the beads and the beads amounting to between 0.5 and 10% by weight of the composition.

11. A composition according to claim 10 wherein beads are from about 500 to about 1,500 microns in diameter and the wall thickness of the beads is between about 210 and 740 microns.

12. A method of treating a surface with an active ingredient comprising:

providing a carrier liquid;

dispersing in the carrier liquid a multiplicity of visible friable beads, each containing from about 0.5 to about 5.0% by weight active ingredients for treating the surface; and massaging the carrier with beads onto the surface for rupturing the beads and discharging the active ingredient to mark the surface with ruptured beads.

13. A method according to claim 12 including providing colorant in the beads for smearing the colorant during rupturing of the beads.

14. A method according to claim 13 including providing essential fragrant oils in the beads as the active ingredient.

15. A method according to claim 13 including providing anti-bacterial liquid as the active ingredient in the beads.

16. A method according to claim 12 including providing the beads to have a diameter of about 500 to about 1,500 microns in diameter and the wall thickness of the beads is between about 210 and 740 microns.

17. A method according to claim 12 including maintaining the beads in the carrier liquid before massaging the carrier with beads to allow the beads to soften in the carrier.

18. A method according to claim 17 including maintaining the beads in the carrier before the massaging step for at least 24 hours.

19. A method of treating a surface with an active ingredient comprising:

providing a carrier liquid;

disbursing in the carrier liquid a multiplicity of visible friable beads, each containing from about 0.5 to about 5.0% by weight active ingredient for treating the surface;

dispensing the carrier with beads through a dispenser pump onto a surface; and using the carrier with beads on the surface, at least one of the steps of dispensing or the step of using the beads on the surface, causing fracturing of the beads to spill their contents and mix it with the carrier liquid, the beads having a different color from the carrier liquid to act as an indicator that the beads have ruptured.

20. A method according to claim 19 including dispensing the carrier liquid with beads through a pump having passages and geometry for rupturing the beads and mixing the active ingredients with the carrier liquid before the carrier liquid leaves the pump.

* * * * *